United States Patent
Kamiya

(10) Patent No.: US 10,070,843 B2
(45) Date of Patent: Sep. 11, 2018

(54) CONTROL DEVICE, RADIOGRAPHIC IMAGING DEVICE, RADIOGRAPHIC IMAGING METHOD AND PROGRAM STORAGE MEDIUM

(71) Applicant: FUJIFILM CORPORATION, Minato-ku, Tokyo (JP)

(72) Inventor: Naokazu Kamiya, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 186 days.

(21) Appl. No.: 15/275,486

(22) Filed: Sep. 26, 2016

(65) Prior Publication Data

US 2017/0086773 A1 Mar. 30, 2017

(30) Foreign Application Priority Data

Sep. 30, 2015 (JP) .................. 2015-195101

(51) Int. Cl.
*A61B 6/00* (2006.01)
*A61B 6/04* (2006.01)
*A61B 6/02* (2006.01)

(52) U.S. Cl.
CPC .............. *A61B 6/54* (2013.01); *A61B 6/025* (2013.01); *A61B 6/0414* (2013.01);
(Continued)

(58) Field of Classification Search
CPC ......... A61B 6/54; A61B 6/502; A61B 6/0414; A61B 6/025; A61B 6/4657; A61B 6/5205; A61B 6/542; A61B 6/465
See application file for complete search history.

(56) References Cited

U.S. PATENT DOCUMENTS

| 7,453,979 B2 * | 11/2008 | Sendai | A61B 6/025 378/23 |
| 2008/0056441 A1 * | 3/2008 | Souchay | A61B 6/025 378/37 |

FOREIGN PATENT DOCUMENTS

| JP | 2007-325796 A | 12/2007 |
| JP | 2008-062058 A | 3/2008 |

(Continued)

OTHER PUBLICATIONS

English language translation of the following: Office Action dated Jun. 5, 2018 from the JPO in a Japanese patent application No. 2015-195101 corresponding to the instant patent application.

*Primary Examiner* — Courtney Thomas
(74) *Attorney, Agent, or Firm* — Solaris Intellectual Property Group, PLLC

(57) ABSTRACT

A control device includes: a radiation source controller that is configured to control a radiation source such that, by moving the radiation source, an incident angle of radiation with respect to a detection face of a radiation detector is plural angles including a first angle where an incident direction of radiation with respect to the detection face is a direction of a normal line to the detection face, and plural second angles different from the first angle; and an imaging controller that is configured to effect control of performing radiographic imaging plural times at a position of the radiation source where the incident angle is the first angle, and performing radiographic imaging a number of times that is less than the plural times at each position of the radiation source where the incident angle is one of the second angles.

11 Claims, 10 Drawing Sheets

(52) U.S. Cl.
CPC ............ *A61B 6/0457* (2013.01); *A61B 6/502* (2013.01); *A61B 6/5205* (2013.01); *A61B 6/542* (2013.01); *A61B 6/465* (2013.01)

(56) References Cited

FOREIGN PATENT DOCUMENTS

| | | |
|---|---|---|
| JP | 2008-513090 A | 5/2008 |
| JP | 2011-125698 A | 6/2011 |
| JP | 2013-013775 A | 1/2013 |

\* cited by examiner

LEFT-RIGHT DIRECTION

CONTROL DEVICE, RADIOGRAPHIC IMAGING DEVICE, RADIOGRAPHIC IMAGING METHOD AND PROGRAM STORAGE MEDIUM

CROSS-REFERENCE TO RELATED APPLICATION

This application claims priority under 35 USC 119 from Japanese Patent Application No. 2015-195101 filed on Sep. 30, 2015, the disclosure of which is incorporated herein by reference in its entirety.

BACKGROUND

Technical Field

The present disclosure relates to a control device, a radiographic imaging device, a radiographic imaging method, and a program storage medium.

Related Art

Generally, radiographic imaging devices are known that perform radiographic imaging for purposes such as medical diagnoses. In these types of radiographic imaging devices, technology is known for performing tomosynthesis imaging by irradiating an imaging subject with radiation from plural different incident angles, and imaging a radiographic image (a projection image) at each of the incident angles.

In tomosynthesis imaging, imaging of plural projection images is performed by radiating an imaging subject with radiation from different incident angles, within a specific range, with respect to a radiation detection face of a radiation detector, generating a synthesized two dimensional image, this being a pseudo two dimensional image, from each of the projection images, and reconstructing the projection images to generate a reconstructed image. Such technology is, for example, described in Japanese National Phase Publication Nos. 2000-515046 and 2014-507250.

However, in the above technology, there is a tendency for noise to be integrated into the synthesized two dimensional image and the reconstructed image generated from the projection images according to the numbers of projection images used for generation. This accordingly makes it difficult, for example, to distinguish between noise and calcification when reading the generated images.

Moreover, since the density resolution is generally low for synthesized two dimensional images and reconstructed images, there are concerns that it is difficult to discern the presence of abnormal findings (for example, a tumor) that greatly absorb radiation.

Moreover, due to the spatial resolution generally being low in synthesized two dimensional images, there are concerns that it is difficult to discern the shape when forming an opinion determining benignancy or malignancy by shape, such as for calcification when the imaging subject is a breast.

SUMMARY

In consideration of the above circumstances, the present disclosure provides a control device, radiographic imaging device, radiographic imaging method, and non-transitory program storage medium capable of improving the quality of finally generated radiographic images.

A first aspect of the present disclosure is a control device including; a radiation source controller that is configured to control a radiation source such that, by moving the radiation source, an incident angle of radiation with respect to a detection face of a radiation detector is plural angles including a first angle where an incident direction of radiation with respect to the detection face is a direction of a normal line to the detection face, and plural second angles different from the first angle; and an imaging controller that is configured to effect control of performing radiographic imaging plural times at a position of the radiation source where the incident angle is the first angle, and performing radiographic imaging a number of times that is less than the plural times at each position of the radiation source where the incident angle is one of the second angles.

In the present aspect, the imaging controller may be configured to increase the number of times of imaging at the first angle as the incident angle range becomes wider.

The control device of the present aspect may further include a generating section that is configured to generate, based on the plural radiographic images that have been imaged, at least one of a reconstructed image or a synthesized two dimensional image.

In the present aspect, the generating section may be configured such that in cases of generating the synthesized two dimensional image, generation is performed by using all of the radiographic images obtained by the imaging, or generation is performed by using only the plural radiographic images obtained by the imaging at the first angle.

In the present aspect, the imaging controller may be configured to stop movement of the radiation source and perform imaging in cases in which imaging of the radiographic image is being performed at a position of the radiation source where the incident angle is the first angle; and the imaging controller may be configured to perform imaging while moving the radiation source in cases in which imaging of the radiographic image is being performed at a position of the radiation source where the incident angle is one of the second angles.

The control device of the present aspect may be configured such that a dose of the radiation radiated from the radiation source onto an imaging subject each time imaging is performed is the same dose at the position of the radiation source where the incident angle is the first angle, as at each of the positions of the radiation source where the incident angle is one of the second angles.

Note that reference to the same dose means a predetermined dose so as to image with the same dose. More specifically, a tube current and radiation time are adjusted, or operation conditions of a phototimer are adjusted to achieve the predetermined dose.

In the control device of the present aspect, the same dose may be employed for a dose of the radiation radiated from the radiation source onto an imaging subject in imaging at each position of the radiation source where the incident angle is one of the second angles, and, from out of the plural times of imaging at a position of the radiation source where the incident angle is the first angle, for a dose of the radiation radiated from the radiation source onto the imaging subject in imaging performed the same number of times as the number of times of imaging at each of the positions of the radiation source where the incident angle is one of the second angles.

Note that reference to the same dose means a predetermined dose so as to image with the same dose. More specifically, a tube current and radiation time are adjusted, or operation conditions of a phototimer are adjusted to achieve the predetermined dose.

In the control device of the present aspect, the number of times of imaging may be one time for each position of the radiation source where the incident angle is one of the second angles.

A second aspect of the present disclosure is a radiographic imaging device including a radiation source that is configured to emit radiation; a radiation detector that is configured to image a radiographic image based on radiation incident to a detection face thereof; and the control device of the first aspect.

A third aspect of the present disclosure is a radiographic imaging method including: moving a radiation source, and controlling an incident angle of radiation with respect to a detection face of a radiation detector so as to be a plural angles including a first angle where an incident direction of radiation with respect to the detection face is a direction of a normal line to the detection face, and plural second angles different from the first angle; and performing radiographic imaging plural times at a position of the radiation source where the incident angle is the first angle, and performing radiographic imaging a number of times that is less than the plural times at each position of the radiation source where the incident angle is one of the second angles.

A fourth aspect of the present disclosure is a non-transitory storage medium storing a program that causes a computer to execute radiographic image acquisition processing including: moving a radiation source, and controlling an incident angle of radiation with respect to a detection face of a radiation detector so as to be plural angles including a first angle where an incident direction of radiation with respect to the detection face is a direction of a normal line to the detection face, and plural second angles different from the first angle; and performing radiographic imaging plural times at a position of the radiation source where the incident angle is the first angle, and performing radiographic imaging a number of times that is less than the plural times at each position of the radiation source where the incident angle is one of the second angles.

The present disclosure is able to provide a control device, a radiographic imaging device, a radiographic imaging method, and a program storage medium capable of improving the quality of finally generated radiographic images

BRIEF DESCRIPTION OF THE DRAWINGS

Exemplary embodiments will be described in detail based on the following figures, wherein.

DETAILED DESCRIPTION

Detailed explanation follows regarding exemplary embodiments, with reference to the drawings. Note that the present exemplary embodiments do no limit the present disclosure. Moreover, reference in the following to "the same" means the same within a margin of error that can be viewed as being the same.

First Exemplary Embodiment

Figure 1:
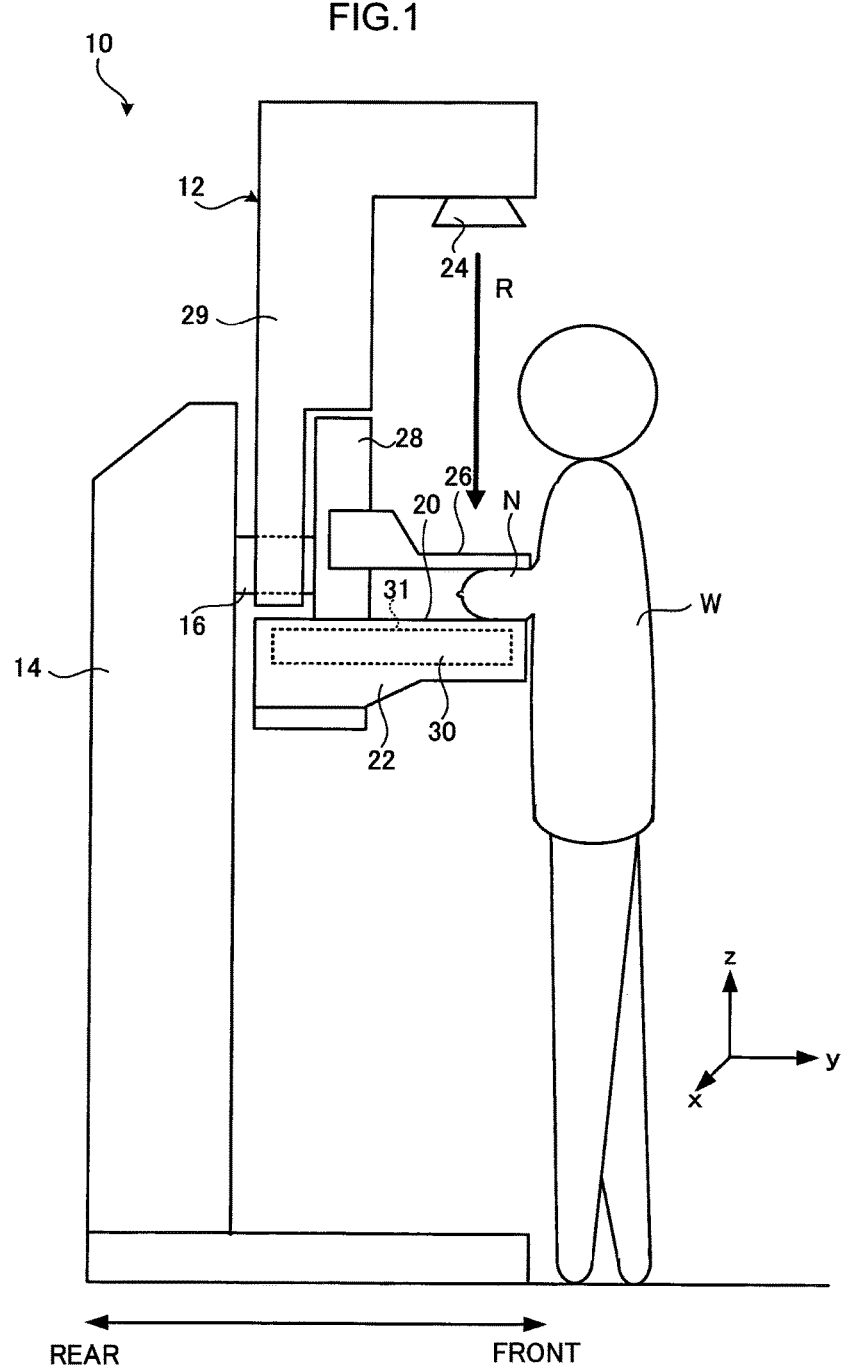
FIG. 1 is a side view illustrating an example of a configuration of a radiographic imaging device according to a first exemplary embodiment.
Figure 2:
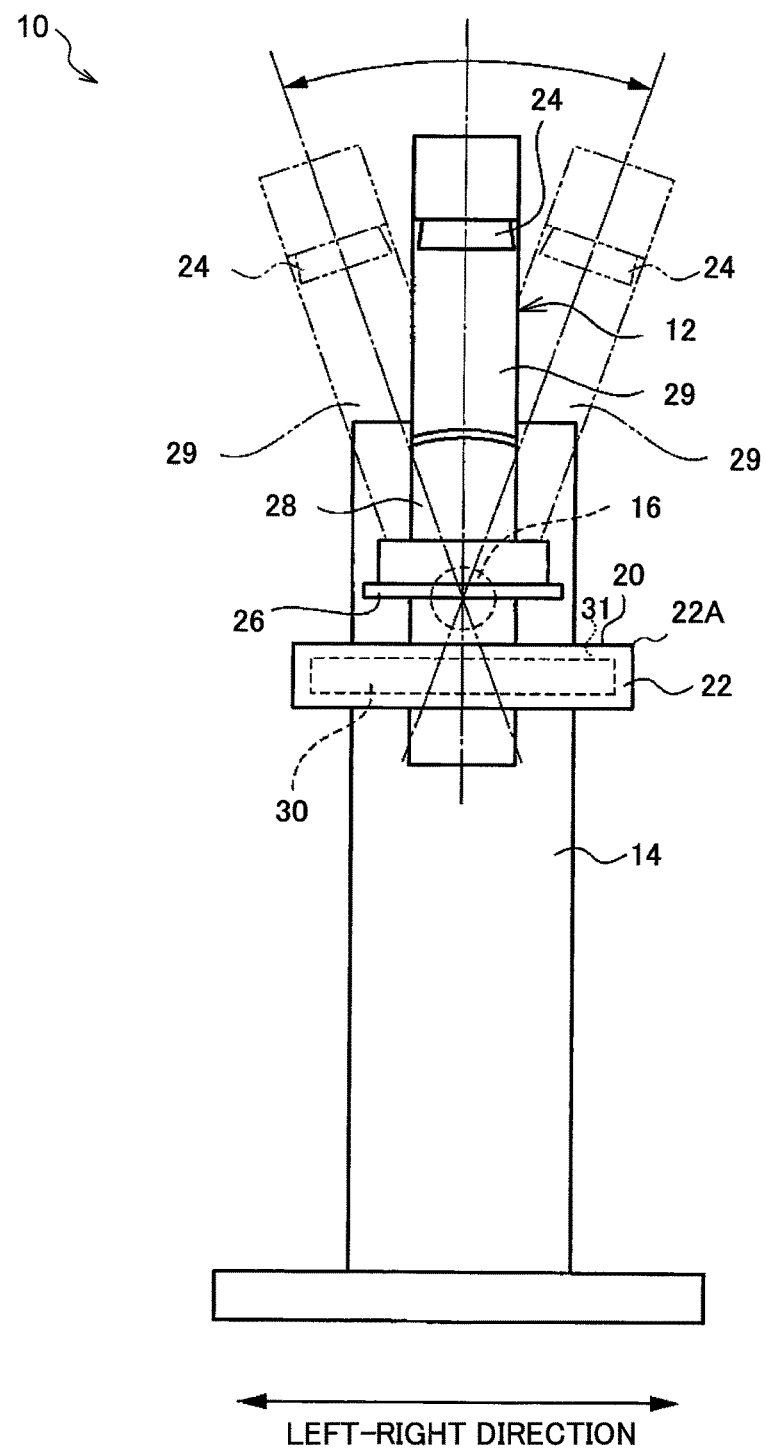
FIG. 2 is a front view illustrating an example of a configuration of the radiographic imaging device illustrated in FIG. 1.
Figure 3:
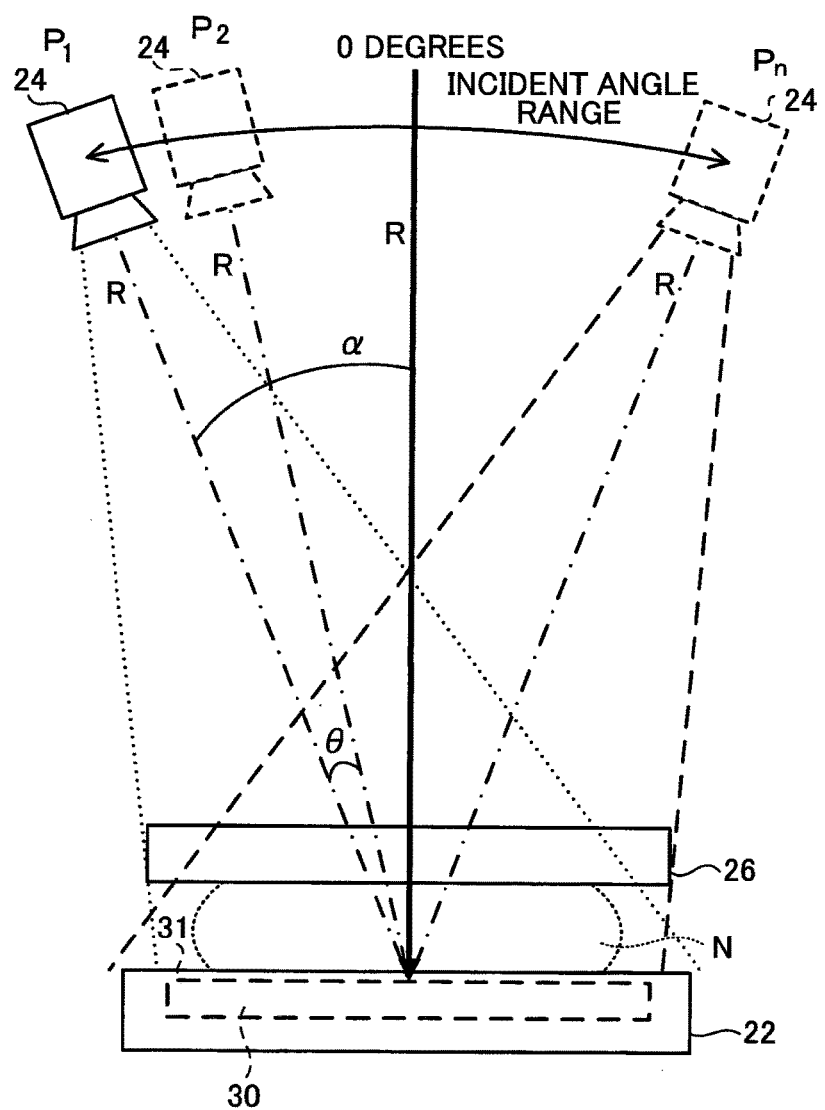
FIG. 3 is a diagram explaining tomosynthesis imaging in the radiographic imaging device according to the first exemplary embodiment.

Explanation first follows regarding a radiographic imaging device according to the present exemplary embodiment. As illustrated in FIG. 1 to FIG. 3, a radiographic imaging device 10 of the present exemplary embodiment is a device that images, as an imaging subject, a breast N of an examinee W using radiation R (for example, X-rays), with the examinee W standing in an upright posture. A specific example of use of the radiographic imaging device 10 is in mammography. In the following, the side near to the examinee W when the examinee W is facing the radiographic imaging device 10 during imaging is referred to as the device front side of the radiographic imaging device 10, the side away from the W when the examinee W is facing the radiographic imaging device 10 is referred to as the device rear side of the radiographic imaging device 10, and the left and right directions of the examinee W when the examinee W is facing the radiographic imaging device 10 are referred to as the device left and right directions of the radiographic imaging device 10 (see each of the arrows in FIG. 1 and FIG. 2).

Note that for the radiographic imaging device 10, a device may be employed that images a breast N of an examinee W in a seated state, seated on a chair (including a wheelchair) or the like.

As illustrated in FIG. 1, the radiographic imaging device 10 includes a measuring section 12 provided at the device front side and having a substantially C-shape in side view, and a base section 14 that supports the measuring section 12 from the device rear side.

The measuring section 12 includes an imaging table 22 formed with a flat imaging face 20 contacted by the breast N of the examinee W in an upright state, a pressing plate 26 for pressing the breast N between itself and the imaging face 20 of the imaging table 22, and a holding section 28 that supports the imaging table 22 and the pressing plate 26. A member that passes through radiation R is employed for the pressing plate 26.

The measuring section 12 includes a radiation source 24 that includes a tube or the like and radiates the radiation R onto the breast N, and a support section 29 that is separate from the holding section 28 and supports the radiation source 24.

A shaft 16 is provided to the measuring section 12, and the measuring section 12 is capable of rotating with respect to the base section 14. The shaft 16 is fixed to the support section 29, and the shaft 16 and the support section 29 rotate as a single unit.

Gears are provided to both the shaft 16 and the holding section 28, and, by switching these gears between a meshed state and an un-meshed state, it is possible to switch between a state in which the holding section 28 and the shaft 16 are coupled together and rotate as a single unit, and a state in which the shaft 16 is separated from the holding section 28 and rotates feely. Note that the switching between transmission and non-transmission of motive force of the shaft 16 is not limited to employing these gears, and various mechanical elements may be employed therefor.

The holding section 28 supports the imaging table 22 and the radiation source 24 with a specific separation between the imaging face 20 and the radiation source 24. The holding section 28 also holds the pressing plate 26, and varies the separation between the pressing plate 26 and the imaging face 20 by sliding the pressing plate 26 along the holding section 28.

From the perspectives of radiation transmissivity and strength, the imaging face 20 contacted by the breast N is, for example, formed from a carbon fiber composite. A radiation detector 30 is disposed inside the imaging table 22 to detect the radiation R that has passed through the breast N and the imaging face 20. The radiation detector 30 generates radiographic images based on the detected radiation R. There are no particular limitations to the type of the radiation detector 30 of the present exemplary embodiment, and, for example, an indirect conversion type of radiation detector may be employed that converts radiation R into light and then converts the converted light into charge, or a direct conversion type of radiation detector may be employed that converts the radiation R directly into charge.

As illustrated in FIG. 2 and FIG. 3, the radiographic imaging device 10 of the present exemplary embodiment is capable of radiating the radiation R from the radiation source 24 within a specific range of different incident angles of the radiation R, and performing imaging from each of the different incident angles (i.e., in tomosynthesis imaging). The "incident angles" referred to here are the angles formed between a normal line to a detection plane 31 of the radiation detector 30 and the radiation axis. Thus, the incident angle is 0 degrees when the normal line and the radiation axis are coincident. In this example, the detection plane 31 of the radiation detector 30 is substantially coplanar to the imaging face 20. Note that for incident angles, an example of a first angle of the present disclosure is 0 degrees, and examples of second angles of the present disclosure are plural angles other than 0 degrees.

In the following, the range of different incident angles for one performance of tomosynthesis imaging is referred to as the "incident angle range". Specific example of the incident angle range are ranges of ±10 degrees, or ±20 degrees, with respect to a normal line to the detection plane 31 of the radiation detector 30. Each of the radiographic images obtained by performing tomosynthesis imaging is referred to as a "projection image".

In the present exemplary embodiment, as illustrated in FIG. 3, the position of the radiation source 24 is moved from an angle α by a specific angle θ each time, and imaging is performed with the position of the radiation source 24 positioned at n locations (imaging positions) from $P_1$ to $P_n$.

In the radiographic imaging device 10 of the present exemplary embodiment, for cases other than an incident angle of 0 degrees, imaging is performed at each imaging position while continuously moving the radiation source 24. As an example of an imaging method of continuously moving the radiation source 24, the radiation source 24 may be moved, and while doing so, without stopping, the radiation source 24 radiates the radiation R onto the breast N each time an imaging position is reached, with imaging by the radiation detector 30 performed in synchronization with the radiation timing.

Next, explanation follows regarding a configuration of a radiographic imaging system 1 of the present exemplary embodiment.

Figure 4:
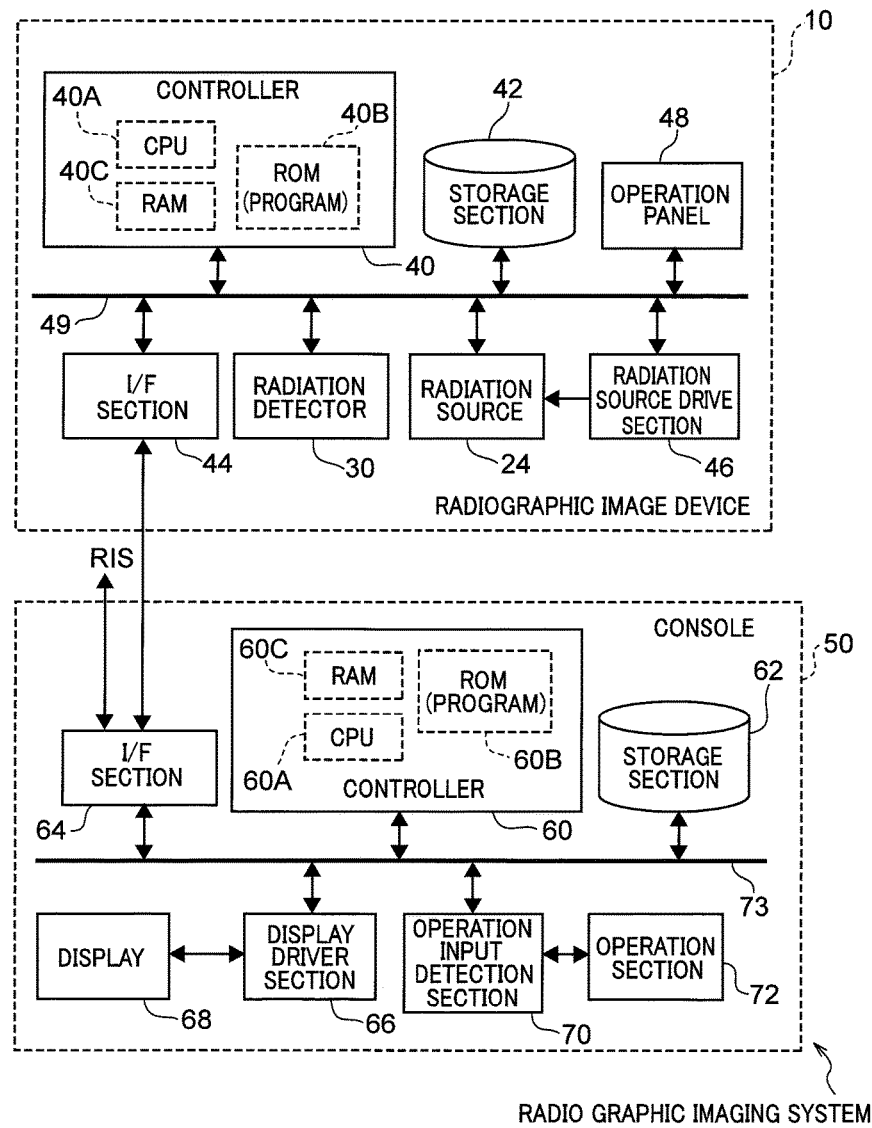
FIG. 4 is a block diagram illustrating an example of a configuration of the radiographic imaging system according to the first exemplary embodiment.

FIG. 4 is a block diagram illustrating an example of a configuration of the radiographic imaging system 1 of the present exemplary embodiment. As illustrated in FIG. 4, the radiographic imaging system 1 of the present exemplary embodiment includes the radiographic imaging device 10 and a console 50.

The console 50 controls the radiographic imaging device 10 using an imaging menu or various other information acquired from, for example, an external system through a Local Area Network (LAN) or the like.

The console 50 of the present exemplary embodiment is a server computer. As illustrated in FIG. 4, the console 50 includes a controller 60, a storage section 62, an interface (I/F) section 64, a display driver section 66, a display 68, an operation input detection section 70, and an operation section 72. The controller 60, the storage section 62, the I/F section 64, the display driver section 66, and the operation input detection section 70 are mutually connected to each other through a bus 73, such as a system bus or a control bus, so as to be capable of exchanging various information with each other.

The controller 60 controls the overall operation of the console 50. The controller 60 of the present exemplary embodiment includes a central processing unit (CPU) 60A, read only memory (ROM) 60B, and random access memory (RAM) 60C. Various processing programs and the like to be executed by the CPU 60A are pre-stored in the ROM 60B. The RAM 60C temporarily stores various data.

Image data of radiographic images imaged by the radiographic imaging device 10, and various other information, are stored in the storage section 62. Specific examples of the storage section 62 include a hard disk drive (HDD) and a solid state drive (SSD).

The I/F section 64 communicates various information between the radiographic imaging device 10 and an external system (such as a radiology information system (RIS)) using wireless communication or wired communication.

The display 68 displays various information. The display driver section 66 controls the display of various information on the display 68.

The operation section 72 is used by a user to input instruction, such as instruction regarding imaging of radiographic images including instruction for radiation R exposure, and to input various information. Note that in the present exemplary embodiment, user refers to a technician or doctor who performs imaging using the radiographic imaging system 1 (the radiographic imaging device 10).

There are no particular limitations to the operation section 72, and examples thereof include various switches, a touch panel, a touch pen, and a mouse. The operation section 72 and the display 68 may also be integrated together as a touch panel display. The operation input detection section 70 detects the operational state of the operation section 72.

The radiographic imaging device 10 of the present exemplary embodiment includes the radiation source 24, the radiation detector 30, a controller 40, a storage section 42, an I/F section 44, a radiation source drive section 46, and an operation panel 48. In the present exemplary embodiment, for example, the radiographic imaging device 10 includes the functionality of the control device of the present disclosure.

The radiation source 24, the radiation detector 30, the controller 40, the storage section 42, the I/F section 44, the radiation source drive section 46, and the operation panel 48 are connected to each other through a bus 49, such as a system bus or a control bus, so as to be capable of exchanging various information between each other.

The controller 40 of the present exemplary embodiment controls the overall operation of the radiographic imaging device 10. The controller 40 controls the radiation source 24 and the radiation detector 30 during imaging of radiographic images. The controller 40 of the present exemplary embodiment includes a CPU 40A, ROM 40B, and RAM 40C. Various programs are pre-stored in the ROM 40B, including an image acquisition processing program and generation processing program, described later, to be executed by the CPU 40A. The RAM 40C temporarily stores various data. In the radiographic imaging system 1 of the present exemplary embodiment, the controller 40 functions as a radiation source controller and an imaging controller by the CPU 40A executing the image acquisition processing program stored on the ROM 40B. The image acquisition processing program of the present exemplary embodiment is an example of a radiographic imaging program of the present disclosure.

Image data of radiographic images from imaging with the radiation detector 30 and various other information is stored in the storage section 42. Specific examples of the storage section 42 include HDDs and SDDs.

The I/F section 44 communicates various information with the console 50 through wireless communication or wired communication.

In the present exemplary embodiment, various programs stored in the controller 40 of the radiographic imaging device 10 and in the controller 60 of the console 50 are pre-stored in the ROM (40B, 60B) of the controller 40 and the controller 60. However, there is no limitation thereto. The various programs may, for example, be stored on a recording medium, such as a compact disk read only memory (CD-ROM) or removable disk, such that the programs are then installed on the ROM (40B, 60B) from the recording medium. Alternatively, the various programs may be installed on the ROM (40B, 60B) from an external device through a communication line, such as the internet.

The radiation source drive section 46 moves the radiation source 24 to a position corresponding to an incident angle by rotating the shaft 16.

The operation panel 48 is provided with functionality to receive a press instruction from a user to raise or lower the pressing plate 26 while clamping the breast N of the examinee W. The operation panel 48 is, for example, provided as plural switches on the imaging table 22 of the radiographic imaging device 10. The operation panel 48 may be provided as a touch panel.

Next, explanation follows regarding operation of the radiographic imaging device 10 of the present exemplary embodiment, with reference to the drawings.

First, explanation follows regarding image acquisition processing performed by the radiographic imaging device 10 of the radiographic imaging system 1 of the present exemplary embodiment.

In the radiographic imaging system 1 of the present exemplary embodiment, in order to start imaging of the breast N of the examinee W, a user instructs start of imaging by using the operation section 72 of the console 50. The instruction, input with the operation section 72, to start imaging is detected with the operation input detection section 70, and sent to the radiographic imaging device 10 through the I/F section 64. The user may also position the breast N of the examinee W on the imaging face 20 of the imaging table 22 of the radiographic imaging device 10.

Figure 5:
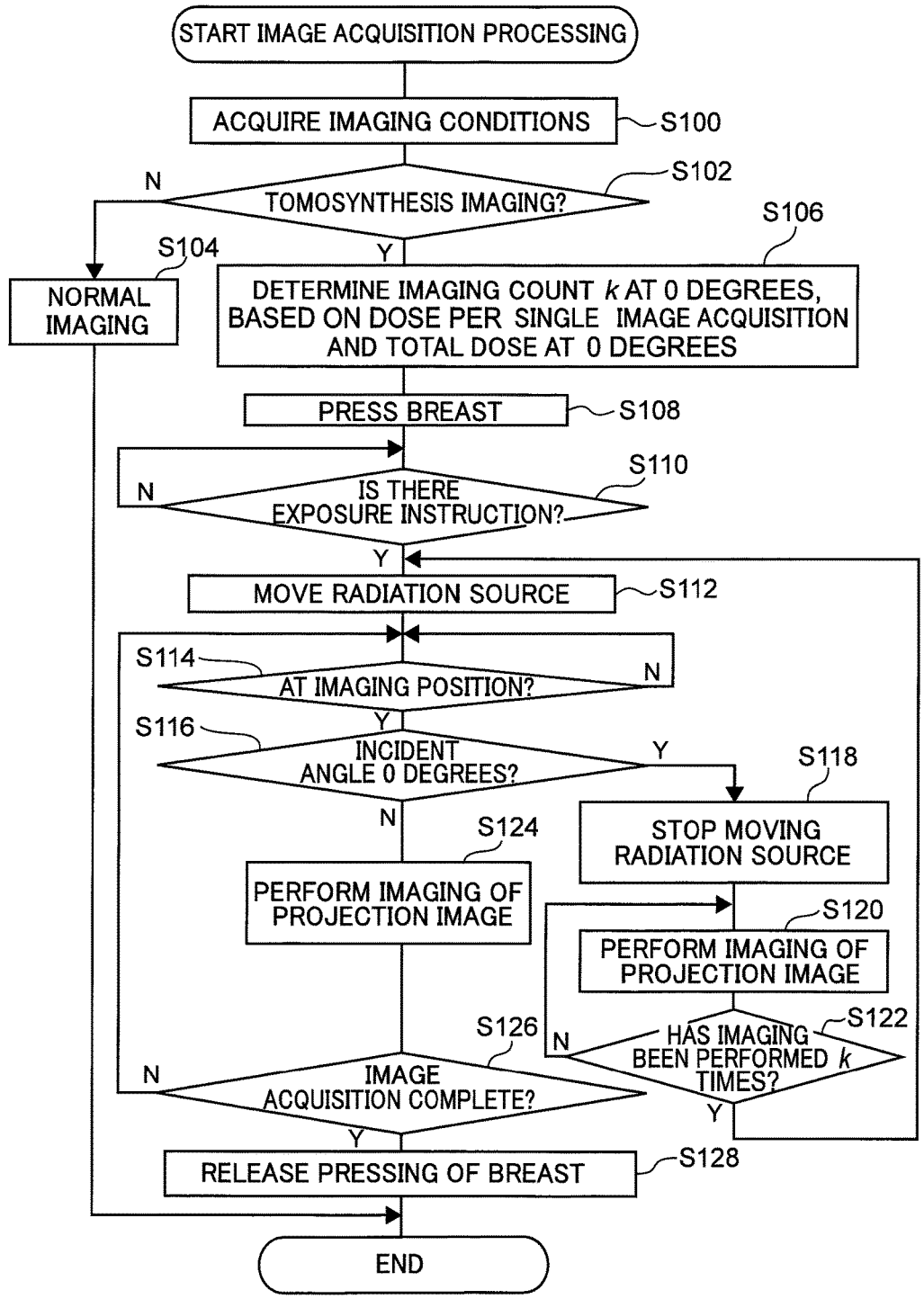
FIG. 5 is flowchart illustrating an example of image acquisition processing performed by the radiographic imaging device according to the first exemplary embodiment.

In the radiographic imaging device 10 of the present exemplary embodiment, the image acquisition processing is executed after an instruction to start radiographic imaging has been received from the console 50 through the I/F section 44. FIG. 5 is a flowchart illustrating an example of the image acquisition processing executed by the controller 40 of the radiographic imaging device 10 of the present exemplary embodiment. In the radiographic imaging device 10, the CPU 40A of the controller 40 executes the image acquisition processing by executing the image acquisition processing program stored in the ROM 40B.

At step S100, the controller 40 acquires imaging conditions. The imaging conditions include conditions for radiation R exposure by the radiation source 24, including information indicating whether the type of imaging to be performed is tomosynthesis imaging or normal imaging (described in detail later), the tube voltage, the tube current, the exposure time, and the dose, and information related to imaging of the radiographic images, such as orientation information. The orientation information in the present exemplary embodiment is information related to the orientation of the radiation source 24, and includes information indicating the imaging position (including incident angles or an incident angle range) of the radiation source 24 when performing tomosynthesis imaging on the breast N.

The imaging conditions are included in the imaging menu as well as imaging subject information related to the examinee W and the breast N. Thus, in cases in which the console 50 acquires the imaging menu from an RIS or the like, the controller 40 acquires the imaging conditions from the console 50 through the I/F section 44. In cases in which the imaging conditions are set by a user, for example using the operation section 72 of the console 50, the controller 40 also acquires the imaging conditions from the console 50 through the I/F section 44.

In cases in which the imaging conditions are pre-stored in the storage section 42 of the radiographic imaging device 10, the controller 40 may acquire the imaging conditions from the storage section 42.

At the next step S102, the controller 40 determines whether or not tomosynthesis imaging is to be performed based on the imaging conditions. In cases in which tomosynthesis imaging is not to be performed, normal imaging is to be performed, negative determination is made, and processing transitions to step S104.

At step S104, the controller 40 performs normal imaging, and then ends the image acquisition processing. In contrast to tomosynthesis imaging, in normal imaging in the present exemplary embodiment, the radiation source 24 is not moved during imaging, and imaging of the radiographic image is performed with the radiation R being radiated from the radiation source 24 onto the breast N in a fixed state of the incident angle. Examples of normal imaging include Cranio-Caudal (CC) imaging and Medio-Lateral Oblique (MLO) imaging.

Although details regarding normal imaging will be omitted, in normal imaging, the breast N is pressed by the pressing plate 26, radiation R is radiated from the radiation source 24 onto the breast N based on the imaging conditions, and after imaging a radiographic image using the radiation detector 30, pressing of the breast N is released.

In cases in which tomosynthesis imaging is determined to be performed, affirmative determination is made at step 102 and processing transitions to step S106.

At step S106, the controller 40 determines an imaging count k that is the number of times of imaging at an incident angle of 0 degrees, based on the dose of radiation R to be emitted from the radiation source 24 for imaging a single projection image (referred to below as "the dose per single image acquisition"), and the total dose of radiation R required for imaging at the imaging position at an incident angle of 0 degrees (referred to below as "the total dose at 0 degrees").

In the present exemplary embodiment, in tomosynthesis imaging, the dose per single image acquisition is predetermined according to the thickness of the breast N or the like, and is the same whatever the imaging position. The total dose at 0 degrees is predetermined according to the quality required for a synthesized two dimensional image, described in detail later.

Based on a value obtained by dividing the total dose at 0 degrees by the dose per single image acquisition, the controller 40 determines the imaging count k at 0 degrees (wherein k=total dose at 0 degrees/dose per single image acquisition, with k being an integer). Since the imaging count k is an integer, the remainder may be rounded up or rounded down in cases in which the total dose at 0 degrees is not exactly divisible by the dose per single image acquisition. It may be determined in advance as to whether to round the remainder up or down based on viewpoints such as the quality of radiographic image, and amount of exposure to the examinee W. In such cases, the amount of exposure to the examinee W is (the number of imaging positions+(k−1))×the dose per single image acquisition.

At the next step S108, the controller 40 moves the pressing plate 26 toward the imaging face 20 according to pressing instruction from a user using the operation panel 48, and presses the breast N. Note that the processing of steps S100 to S102 may be performed after the breast N has been pressed; however, performing these steps prior to pressing the breast N, as in the present exemplary embodiment, enables the time that the breast N is being pressed to be shortened.

When the breast N is pressed by the processing of step S108, the user instructs exposure instruction from the console 50 using the operation section 72.

At the next step S110, the controller 40 determines whether or not an exposure instruction has been given. Negative determination is made and a standby state is adopted until an exposure instruction is given. However, affirmative determination is made after an exposure instruction has been given, and processing transitions to step S112.

Figure 6:
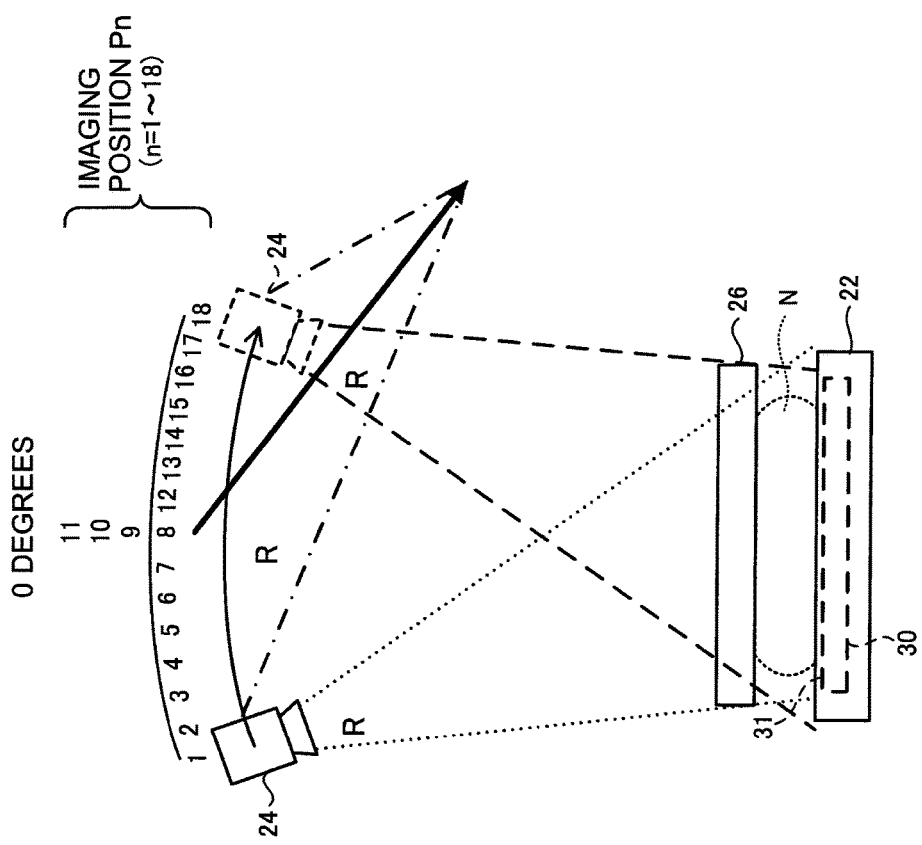
FIG. 6 is front view explaining tomosynthesis imaging according to the first exemplary embodiment.

At step S112, the controller 40 starts moving the radiation source 24 using the radiation source drive section 46. FIG. 6 illustrates a front face view for explaining tomosynthesis imaging in the present exemplary embodiment. The example in FIG. 6 illustrates a case in which the total imaging count is eighteen times, and imaging of projection images is performed at imaging positions $P_1$ to $P_{18}$. Note that in this example projection images are imaged four times at the imaging position of an incident angle of 0 degrees (imaging count k=4). Thus, the imaging positions $P_8$ to $P_{11}$ are the same position.

In such cases, first, movement of the radiation source 24 is started toward the first imaging position. In the example illustrated in FIG. 6, movement of the radiation source 24 is started toward the imaging position $P_1$.

At the next step S114, the controller 40 determines whether or not the radiation source 24 has been moved to the first imaging position. Negative determination is made while the radiation source 24 has not yet been moved to the first imaging position, and a standby state is adopted. Affirmative determination is made after the radiation source 24 has moved to the first imaging position, and processing transitions to step S116.

At step S116, the controller 40 determines whether or not the current incident angle of radiation R by the radiation source 24 is at the 0 degrees imaging position. Negative determination is made in cases in which the incident angle is not that of the 0 degrees imaging position, and processing transitions to step S124. In the example illustrated in FIG. 6, negative determination is made after starting tomosynthesis imaging and the imaging positions are $P_1$ to $P_7$.

At step S124, the controller 40 images a projection image. More specifically, the controller 40 controls emission of radiation R from the radiation source 24 toward the breast N, and controls the radiation detector 30 to image the projection image. The projection image generated by imaging using the radiation detector 30 is stored by the controller 40 in the storage section 42, in association with the incident angle of the radiation R, after being subject to any required processing, such as gain correction, offset correction, and pixel defect correction. A raw image format (RAW image format), for example, may be employed as the format of the generated projection image.

After a projection image has been imaged, at the next step S126, the controller 40 determines whether or not imaging (tomosynthesis imaging) is complete. Negative determination is made in cases in which imaging of projection images has not yet been performed at all the imaging positions, and processing returns to step S114. Note that when execution of the processing of step S114 is subsequently repeated, determination is made at each imaging position as to whether or not the radiation source 24 has moved as far as each position, from imaging position $P_2$ onward.

Thus, after tomosynthesis imaging has been started, first the processing of steps S114, S116, S124, and S126 are repeated, from the imaging start position (the first imaging position $P_1$) until the incident angle of the radiation R of the imaging position is just before 0 degrees (the imaging position $P_7$).

In cases in which the incident angle of the imaging position is 0 degrees (imaging position $P_8$), affirmative determination is made at step S116, and processing transitions to step S118.

At step S118, the controller 40 stops moving the radiation source 24 with the radiation source drive section 46.

At the next step S120, the controller 40 images a projection image in a similar manner to at step S124. After imaging of this projection image has been completed, processing then transitions to step S122.

At step S122, the controller 40 determines whether or not imaging of projection images has been performed k times (k=4 in the example illustrated in FIG. 6) at the imaging position having the incident angle of 0 degrees. Negative determination is made in cases in which the imaging count has not yet reached k, processing returns to step S120, and imaging of a projection image is repeated. In cases in which the imaging count has reached k times, affirmative determination is made and processing returns to step S112.

In such cases, at step S112, the controller 40 restarts moving the radiation source 24 using the radiation source drive section 46, repeats the processing of step S114 to S126, and images projection images at the imaging positions subsequent to the incident angle of 0 degrees. In the example illustrated in FIG. 6, negative determination is made at step S126 for the imaging positions subsequent to the imaging of the projection images at the incident angle of 0 degrees, at imaging positions from $P_{12}$ to $P_{18}$.

After imaging of projection images has been performed at all of the imaging positions, affirmative determination is made at step S126, and processing transitions to step S128.

At step S128, the controller 40 releases the pressing of the breast N by the pressing plate 26. More specifically, the controller 40 releases pressing of the breast N by the pressing plate 26 by moving the pressing plate 26 in the direction away from the imaging face 20, and then ends the image acquisition processing. In the radiographic imaging system 1 of the present exemplary embodiment, after the image acquisition processing has been completed in the radiographic imaging device 10, the radiographic images obtained by imaging (the projection images and the like stored in the storage section 42) are transmitted to the console 50, and stored in the storage section 62 of the console 50. The obtained radiographic images may continue to be stored in the storage section 42 after being transmitted to the console 50, or may be erased from the storage section 42.

In the radiographic imaging system 1 of the present exemplary embodiment, a synthesized two dimensional image or a reconstructed image is generated and displayed based on the projection images obtained by the image acquisition processing described above.

Note that in the present exemplary embodiment a "synthesized two dimensional image" means a pseudo two dimensional image generated by synthesizing projection images. Moreover, a "reconstructed image" may be referred to as a tomographic image, and a tomographic image is reconstructed based on projection images. The projection images, the synthesized two dimensional image, and the reconstructed image are collectively referred to below as "radiographic images".

The generation processing of the synthesized two dimensional image or the reconstructed image may be performed in either the radiographic imaging device 10 or the console 50; however, in the present exemplary embodiment, explanation will be given regarding a case in which the radiographic imaging device 10 performs the generation processing. In cases in which the radiographic imaging device 10 performs the generation processing, the controller 40 functions as a generating section by the CPU 40A executing a generation processing program stored in the ROM 40B.

Next, explanation follows regarding the generation processing performed by the radiographic imaging device 10 in the present exemplary embodiment. Note that there are no particular limitations to the timing at which the generation processing is performed, and the generation processing may be performed following the completion of the image acquisition processing, or the generation processing may be performed at any timing after completion of the image acquisition processing, such as after an instruction to execute the generate processing is received from a user by using the operation panel 48 or the operation section 72.

Figure 7:
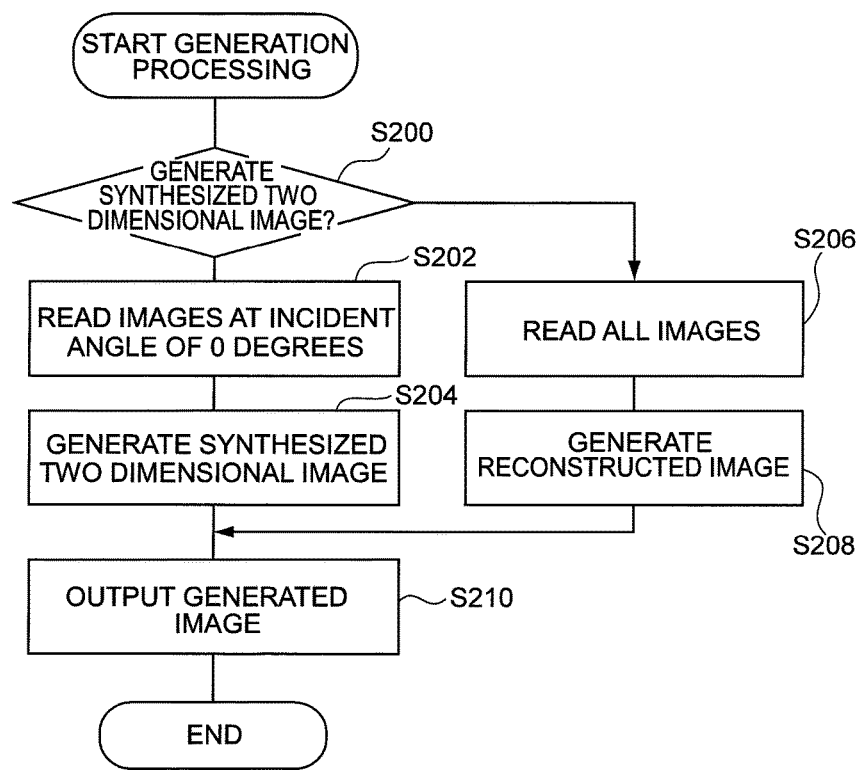
FIG. 7 is a flowchart illustrating an example of generation processing performed by the radiographic imaging device according to the first exemplary embodiment.

FIG. 7 is a flowchart illustrating an example of the generation processing executed by the controller 40 in the radiographic imaging device 10 of the present exemplary embodiment.

At step S200, the controller 40 determines whether or not to generate a synthesized two dimensional image. Whether to generate a synthesized two dimensional image or a reconstructed image may be instructed by a user, such as by using the operation panel 48, or may be automatically selected according to conditions related to the information included in the imaging menu or the like. Negative determination is made in cases in which a synthesized two dimensional image is not to be generated (in cases in which a reconstructed image is to be generated), and processing transitions to step S206.

At step S206, the controller 40 reads all of the projection images stored in the storage section 42.

At the next step S208, the controller 40 uses all the projection images read at step S206, generates a reconstructed image, and then processing transitions to step S210. There are no particular limitations to the method of generating the reconstructed image, and any known reconstruction method may be employed. Specific examples of methods for generating a reconstructed image may include a shift-and-add method, as well as other known computed tomography (CT) reconstruction methods. For example, a typical method of filtered back projection (FBP) may be employed as the CT reconstruction method. An FBP method is a reconstruction method using an extended filtered back projection method in which tomographic scanning in parallel plane slices is performed as part of cone beam CT scanning. Moreover, the iterative reconstruction method described in JP-A No. 2011-125698 may be employed as the reconstruction method. This iterative reconstruction method is also a reconstruction method for CT; however, similarly to in an FBP method, it may also be applied for reconstruction in tomosynthesis imaging.

Affirmative determination is made at step S200 in cases in which synthesized two dimensional images are to be generated, and processing transitions to step S202.

At step S202, the controller 40 reads only the projection images at an incident angle of 0 degrees from the projection images stored in the storage section 42. In the example illustrated in FIG. 6, four projection images imaged at the imaging positions $P_8$ to $P_{11}$ are read from the storage section 42.

At the next step S204, the controller 40 uses the projection images read at step S202 to generate a synthesized two dimensional image, and then processing transitions to step S210. There are no particular limitations to the method of generating the synthesized two dimensional image, and a known method for generating synthesized two dimensional images may be employed therefor.

At step S210, the controller 40 outputs the generated image (the reconstructed image or the synthesized two dimensional image) through the I/F section 44 to the console 50, and then ends the generation processing. Note that there are no particular limitations to the output destination of the reconstructed image or the synthesized two dimensional image, and it may be a destination other than the console 50. Alternatively, configuration may be made such that the generated image is not output to an external device from the radiographic imaging device 10, and is stored in the storage section 42. In cases in which the reconstructed image or the synthesized two dimensional image is output to the console 50, the console 50 stores the input reconstructed image or synthesized two dimensional image in the storage section 62, and also displays the reconstructed image or the synthesized two dimensional image on the display 68.

Note that in the generation processing described above, explanation has been regarding a case in which one of a reconstructed image or a synthesized two dimensional image is generated; however, both a reconstructed image and a synthesized two dimensional image may be generated. In such cases, configuration may be made such that the processing of step S200 is not performed, the processing of steps S206, S208 is performed prior to the processing of step S202 or after the processing of step S204, and then the synthesized two dimensional image and the reconstructed image generated at step S210 are output.

Figure 8:
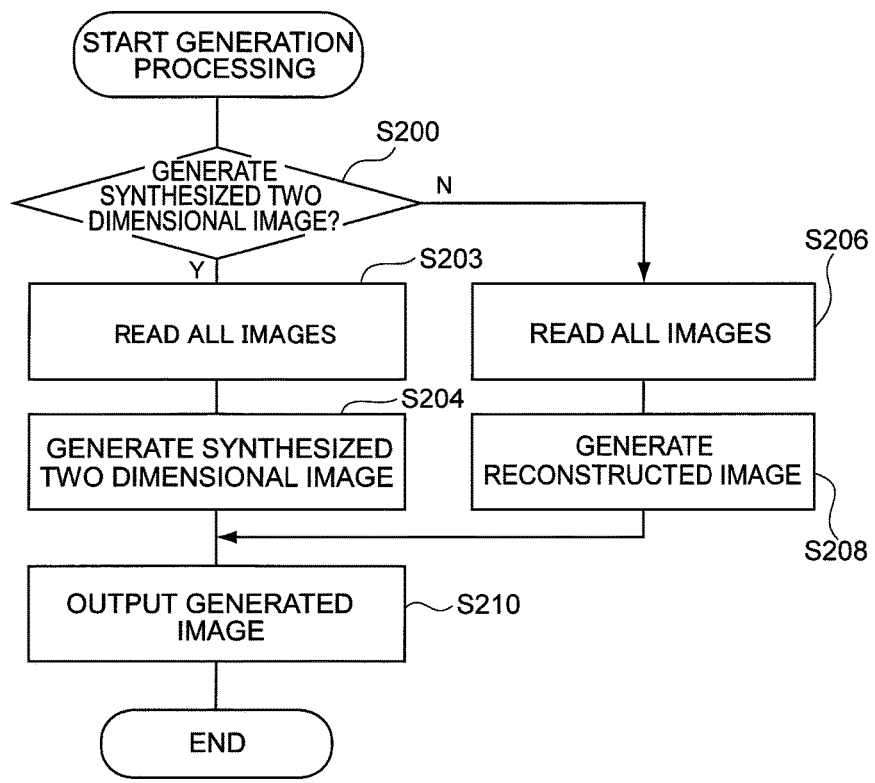
FIG. 8 is a flowchart illustrating another example of generation processing performed by the radiographic imaging device according to the first exemplary embodiment.

Moreover, although in the generation processing the synthesized two dimensional image is generated based on the projection images imaged at the imaging position with incident angle of 0 degrees, the synthesized two dimensional image may be generated based on all of the projection images. FIG. 8 is a flowchart illustrating an example of the generation processing executed by the controller 40 of the radiographic imaging device 10 in such cases. In the generation processing illustrated in FIG. 8, step S203 is executed in place of step S202 of the generation processing illustrated in FIG. 7.

In the generation processing illustrated in FIG. 8, in order to generate a synthesized two dimensional image (in cases in which affirmative determination has been made at step S200), at step S203, the controller 40 reads all the projection images stores in the storage section 42. Then, at the next step S204, the controller 40 uses all of the projection images read at step S203 to generate a synthesized two dimensional image. In such cases, similarly to at step S204 of FIG. 7, there are no particular limitations to the method of generating the synthesized two dimensional image.

In such cases in which the synthesized two dimensional image is generated based on all of the projection images, the image quality is improved more than that of a synthesized two dimensional image generated using only the projection images imaged at the imaging position of the incident angle of 0 degrees, due to there being a larger volume of information. However, the time for generation can be shortened in cases in which the synthesized two dimensional image is generated based only on the projection images imaged at the imaging position of an incident angle of 0 degrees. Moreover, in this case, the synthesized two dimensional image can be generated without waiting for completion of tomosynthesis imaging (without waiting for completion of imaging at all of the imaging positions).

Second Exemplary Embodiment

Next, explanation follows regarding a second exemplary embodiment. Note that parts that are similar to the radiographic imaging system 1 and the radiographic imaging device 10 according to the first exemplary embodiment are allocated the same reference numerals, and detailed explanation thereof is omitted. Image acquisition processing with the radiographic imaging device 10 of the present exemplary embodiment differs from that of the first exemplary embodiment.

The configuration of the radiographic imaging system 1 and the radiographic imaging device 10 is similar to that of the radiographic imaging system 1 and the radiographic imaging device 10 of the first exemplary embodiment (see FIG. 1 to FIG. 4) and, therefore, explanation thereof is omitted.

In the present exemplary embodiment, part of the image acquisition processing performed by the radiographic imaging device 10 differs and, therefore, explanation will be given regarding the different processing.

In the radiographic imaging device 10 of the present exemplary embodiment, imaging count k at the imaging position of an incident angle of 0 degrees differs according to the size of the incident angle range during tomosynthesis imaging. More specifically, the imaging count k increases the larger (wider) the incident angle range is.

The resolution of the reconstructed image generated using the projection images differs according to the incident angle range in tomosynthesis imaging. Note that in the present exemplary embodiment, "resolution" means resolution in a direction of a normal line to the reconstructed image (the depth direction), and means the resolution in a direction of a normal line to the detection plane 31 of the radiation detector 30. The resolution of the reconstructed image is higher the larger the incident angle range.

Thus, tomosynthesis imaging with large incident angle range is performed in cases in which a thorough examination is being performed, and high quality radiographic images (including synthesized two dimensional images and reconstructed images) are desired. In the radiographic imaging device 10 of the present exemplary embodiment, by increasing the imaging count k as the incident angle range gets larger (wider), the total dose at 0 degrees can be made to be a larger proportion of the overall dose during tomosynthesis imaging, noise can be reduced, and the quality of the synthesized two dimensional images and the reconstructed images is thereby raised.

Figure 9:
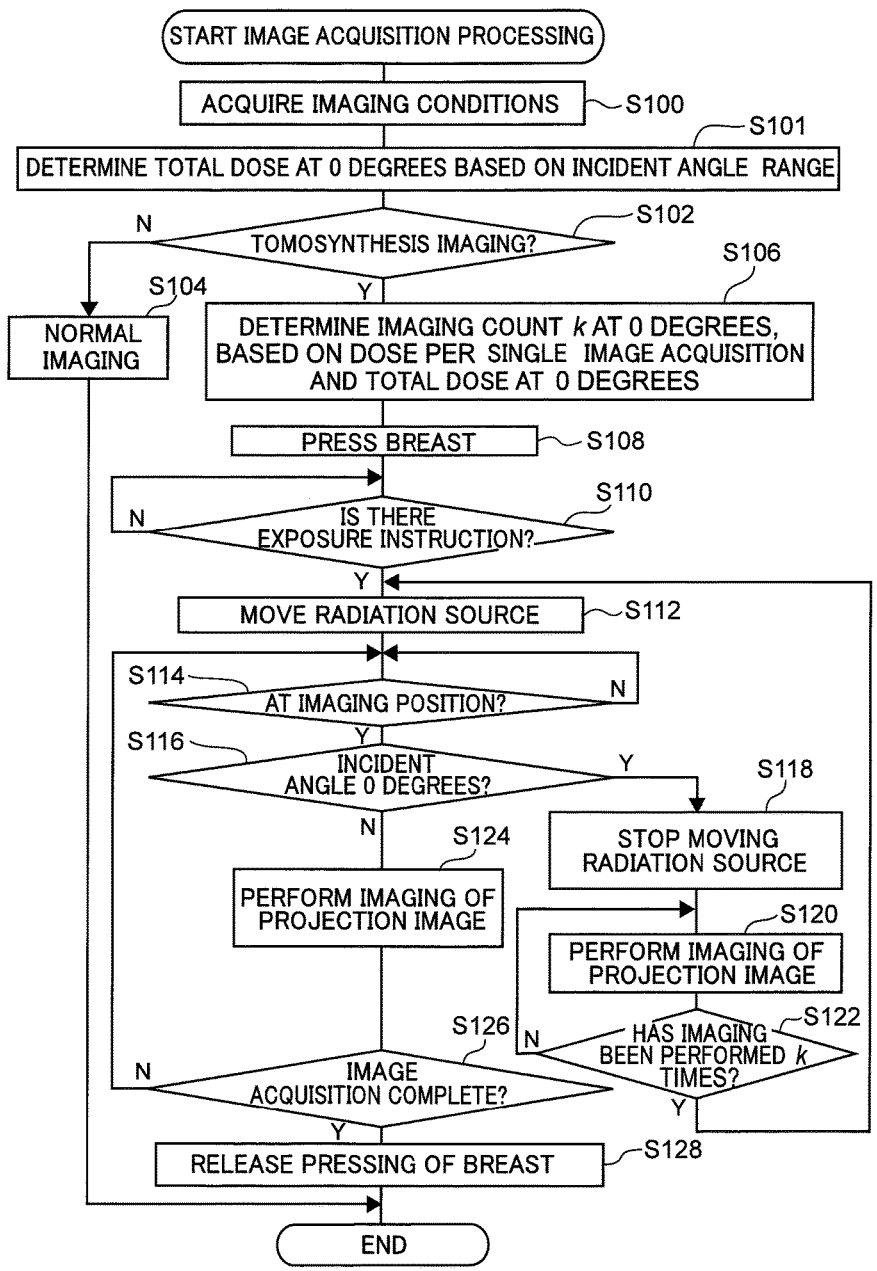
FIG. 9 is a flowchart illustrating an example of image acquisition processing performed by a radiographic imaging device according to a second exemplary embodiment.

Explanation follows regarding image acquisition processing of the radiographic imaging device 10 of the present exemplary embodiment. FIG. 9 is a flowchart illustrating an example of a flow of the image acquisition processing executed by the controller 40 of the radiographic imaging device 10 of the present exemplary embodiment.

In the image acquisition processing of the present exemplary embodiment illustrated in FIG. 9, step S101 is added between step S100 and step S102 in the image acquisition processing of the first exemplary embodiment (see FIG. 5).

At step S101, the controller 40 determines the total dose at 0 degrees based on the incident angle range. In the radiographic imaging system 1 of the present exemplary embodiment, correspondence relationships between incident angle ranges and total dose at 0 degrees are predetermined and stored in advance in the storage section 42 or the storage section 62. Thus, the controller 40 determines the total dose at 0 degrees corresponding to the incident angle range contained in the imaging conditions acquired at step S100, based on the correspondence relationships stored in the storage section 42 or the storage section 62. Step S101 may be omitted in cases in which the total dose at 0 degrees is contained in the imaging conditions.

By determining the total dose at 0 degrees in this manner, the imaging count k at the imaging position of an incident angle of 0 degrees that is determined at step S106 may be a number of times that accords with the size of the incident angle range.

Figure 10:
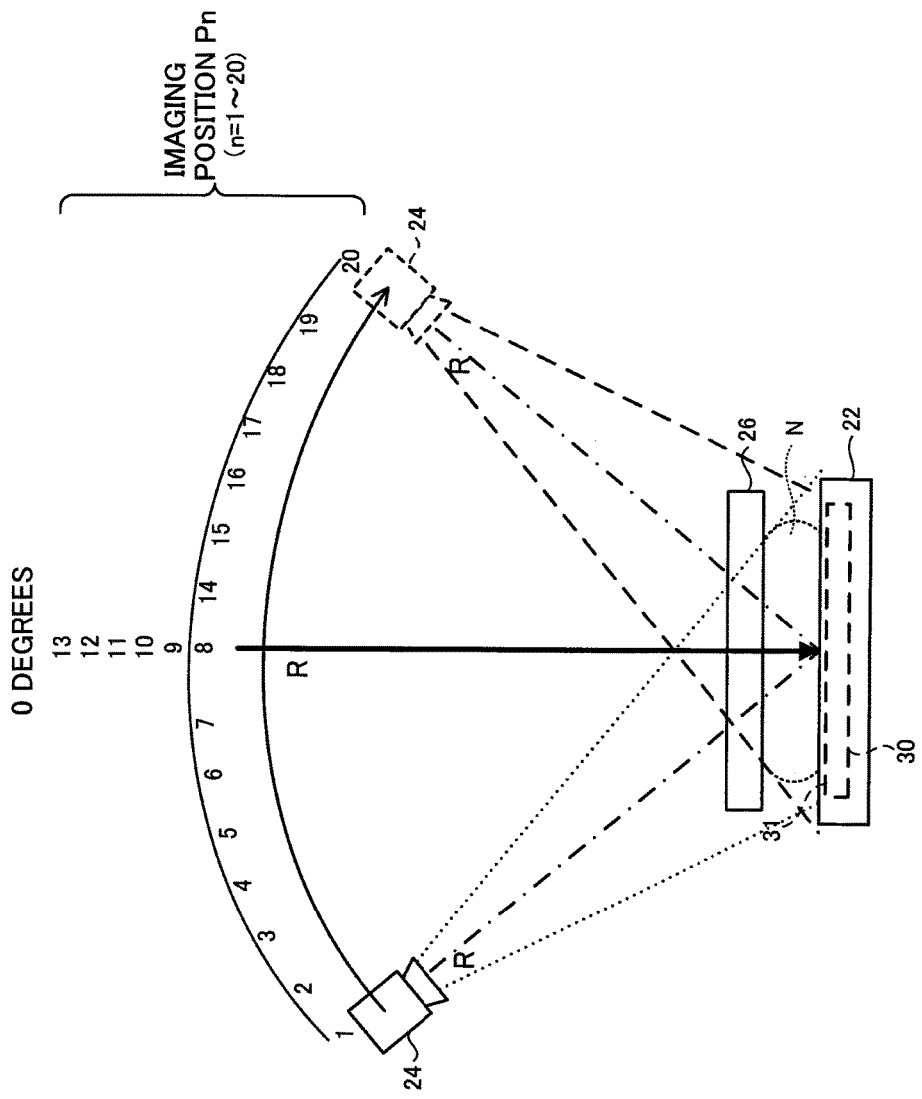
FIG. 10 is a front view to explain tomosynthesis imaging according to the second exemplary embodiment.

FIG. 10 is a front view for explaining tomosynthesis imaging in cases in which the incident angle range is large (larger than in the first exemplary embodiment (see FIG. 6)). The example in FIG. 10 illustrates a case in which the total imaging count is twenty times, and projection images are imaged at imaging positions $P_1$ to $P_{20}$. FIG. 10 illustrates a case in which imaging of projection images is performed six times at the imaging position of an incident angle of 0 degrees (imaging count k=6). Thus, the imaging positions $P_8$ to $P_{13}$ are the same position.

In the present exemplary embodiment, the specific angle θ by which the radiation source 24 is moved (see FIG. 3) differs according to the incident angle range; however, the number of different imaging positions (the number of times of image acquisition after excluding the superimposed count at the imaging position of an incident angle of 0 degrees) is the same irrespective of the incident angle range.

A state is accordingly achieved in which plural projection images have been imaged by executing the above image acquisition processing, and stored in the storage section 42.

The processing to generate the synthesized two dimensional image or reconstructed image using the projection images is similar to the generation processing of the first exemplary embodiment (see FIG. 7, FIG. 8), and so explanation thereof is omitted.

In the radiographic imaging device 10 of each of the exemplary embodiments explained above, the controller 40 moves the radiation source 24, and the incident angle of the radiation R with respect to the detection plane 31 of the radiation detector 30 is controlled to plural angles, including a first angle (0 degrees) in which the incident direction of the radiation R with respect to the detection plane 31 is the direction of a normal line to the detection plane 31, and plural second angles that are different from the first angle. The controller 40 controls so as to perform radiographic imaging plural times (k times) at the position of the radiation source 24 where the incident angle is the first angle (0 degrees), and to image a radiographic image a number of times, less than the k times, at each position of the radiation source 24 where the incident angle is at a second angle.

Thus, in the radiographic imaging device 10 of each of the exemplary embodiments described above, the total dose at 0 degrees can be made to be a larger proportion of the overall dose during tomosynthesis imaging, enabling noise to be reduced, and thereby improving the quality of the finally generated radiographic images (the synthesized two dimensional image and the reconstructed image). The proportion of the total dose at 0 degrees to the overall dose can be freely set.

Moreover, due to the total dose at 0 degrees being larger, the signal-to-noise ratio (S/N ratio, signal strength) of the radiographic images at 0 degrees (the total of the projection images at 0 degrees) can be raised. This thereby facilitates noticing a weak signal, such as of calcification, and facilitates discerning the shape in cases in which forming an opinion determining benignancy or malignancy by shape.

Moreover, in each of the above exemplary embodiments, in cases in which imaging is performed at a position where the incident angle of the radiation R is 0 degrees, imaging is performed with the radiation R being emitted in a state in which movement of the radiation source 24 has been stopped, instead of imaging with the radiation R being emitted while the radiation source 24 is being moved. Thus, due to not moving the radiation source 24 while the radiation R is being emitted, there is no blurring in the projection images (no streaking in the images), and the quality of the radiographic images can be improved. Moreover, at positions where the incident angle of the radiation R is not 0 degrees, imaging is performed with the radiation R being emitted while moving the radiation source 24, and therefore tomosynthesis imaging can be performed faster than cases in which the radiation source 24 is stopped at the imaging positions.

Moreover, in each of the above exemplary embodiments, the projection images obtained during a single time of tomosynthesis imaging may be employed to generate both the synthesized two dimensional image and the reconstructed image. This thereby enables the exposure dose of the examinee W to be reduced compared to cases in which imaging of radiographic images (projection images) is performed separately to generate the synthesized two dimensional image and the reconstructed image, respectively.

In each of the above exemplary embodiments, explanation has been given of cases in which tomosynthesis imaging is performed while the radiation source 24 is continuously moved; however, there is no limitation thereto, and tomosynthesis imaging may be performed while intermittently moving the radiation source 24. As a method of imaging while moving the radiation source 24 intermittently, for example, a cycle may be repeatedly performed in which the radiation source 24 is moved to each of the imaging positions, temporarily stopped, and the radiation R is emitted from the radiation source 24. Alternatively, a cycle may be repeatedly performed in which the radiation R is emitted from the radiation source 24 when each of the imaging positions is reached while moving the radiation source 24, and then, after temporarily stopping, the radiation source 24 is moved again.

Note that in each of the above exemplary embodiments, the imaging count k at the incident angle of 0 degrees is determined according to the total dose at 0 degrees; however, the imaging count k may be predetermined according to the incident angle range, and included in the imaging conditions.

Note that, in the each of the above exemplary embodiments, the dose for imaging each time are the same irrespective of the imaging position; however, the dose for imaging each time at the imaging position of the incident angle of 0 degrees may be different from the dose at the imaging positions of other incident angles. Preferably the dose for at least one time of the image acquisitions at the imaging position of the incident angle of 0 degrees is the same as the dose at an imaging position of another incident angle. In particular, the algorithm for generating the reconstructed image can be simplified by making the dose of all image acquisitions the same, as in the above exemplary embodiments.

Explanation has been given in the second exemplary embodiment of a case in which the number of different imaging positions (the number of times of image acquisition after excluding the superimposed count at the imaging position of the incident angle of 0 degrees) is the same irrespective of the incident angle range; however, the number of different imaging positions may vary according to the incident angle range. For example, the number of different imaging positions may be increased as the incident angle range gets larger by setting the specific angle θ on which the imaging positions (the movement of the radiation source 24) are based as the same, irrespective of the incident angle range. In such cases, the imaging count k at 0 degrees may be varied according to the number of different imaging positions (for example, the imaging count k can be increased the greater the number of different imaging positions).

In the above exemplary embodiments, imaging of a projection image is performed one time (one frame) at the imaging positions other than the imaging position of an incident angle of 0 degrees; however, there is no limitation to the number of times of the imaging being one time, and the imaging may be performed plural times as long as it is a smaller number of times than the imaging count k at 0 degrees.

Explanation has been given in each of the above exemplary embodiments of cases in which the radiographic imaging device 10 is equipped with the functionality of the radiation source controller, the imaging controller, and the generating section; however, the console 50, or an external controller different from the radiographic imaging device 10 or the console 50, may be equipped with part of, or all of, the functionality of each section.

In the radiographic imaging device 10 of each of the above exemplary embodiments, the breast N of the examinee W is the imaging subject; however, the imaging subject is not limited to the breast N, and, for example, another site on a human body, or a living organism other than a human, or an object (inorganic object), may be the imaging subject.

There are no particular limitations to the radiation R in each of the above exemplary embodiments, and X-rays, gamma-rays, or the like may be applied therefor.

The configurations and operations of the radiographic imaging system 1, the radiographic imaging device 10, the console 50 explained in the above exemplary embodiments are merely examples, and obviously modifications thereto are possible according to the circumstances, within a range not departing from the spirit of the present disclosure.

What is claimed is:

1. A control device comprising:
a radiation source controller that is configured to control a radiation source such that, by moving the radiation source, an incident angle of radiation with respect to a detection face of a radiation detector is a plurality of angles including a first angle where an incident direction of radiation with respect to the detection face is a direction of a normal line to the detection face, and a plurality of second angles different from the first angle; and
an imaging controller that is configured to effect control of performing radiographic imaging a plurality of times at a position of the radiation source where the incident angle is the first angle, and performing radiographic imaging a number of times that is less than the plurality of times at each position of the radiation source where the incident angle is one of the second angles.

2. The control device of claim 1, wherein:
the imaging controller is configured to increase the number of times of imaging at the first angle as the incident angle range becomes wider.

3. The control device of claim 1, further comprising a generating section that is configured to generate, based on the plurality of radiographic images that have been imaged, at least one of a reconstructed image or a synthesized two dimensional image.

4. The control device of claim 3, wherein:
the generating section is configured such that in cases of generating the synthesized two dimensional image, generation is performed by using all of the radiographic images obtained by the imaging, or generation is performed by using only the plurality of radiographic images obtained by the imaging at the first angle.

5. The control device of claim 1, wherein:
the imaging controller is configured to stop movement of the radiation source and perform imaging in cases in which imaging of the radiographic image is being performed at a position of the radiation source where the incident angle is the first angle; and
the imaging controller is configured to perform imaging while moving the radiation source in cases in which imaging of the radiographic image is being performed at a position of the radiation source where the incident angle is one of the second angles.

6. The control device of claim 1, wherein a dose of the radiation radiated from the radiation source onto an imaging subject each time imaging is performed is the same dose at the position of the radiation source where the incident angle is the first angle, as at each of the positions of the radiation source where the incident angle is one of the second angles.

7. The control device of claim 1, wherein the same dose is employed:
for a dose of the radiation radiated from the radiation source onto an imaging subject in imaging at each position of the radiation source where the incident angle is one of the second angles; and,
from out of the plurality of times of imaging at a position of the radiation source where the incident angle is the first angle, for a dose of the radiation radiated from the radiation source onto the imaging subject in imaging performed the same number of times as the number of times of imaging at each of the positions of the radiation source where the incident angle is one of the second angles.

8. The control device of claim 1, wherein the number of times of imaging is one time for each position of the radiation source where the incident angle is one of the second angles.

9. A radiographic imaging device comprising:
a radiation source that is configured to emit radiation;
a radiation detector that is configured to image a radiographic image based on radiation incident to a detection face thereof; and
the control device of claim 1.

10. A radiographic imaging method comprising:
moving a radiation source, and controlling an incident angle of radiation with respect to a detection face of a radiation detector so as to be a plurality of angles including a first angle where an incident direction of radiation with respect to the detection face is a direction of a normal line to the detection face, and a plurality of second angles different from the first angle; and
performing radiographic imaging a plurality of times at a position of the radiation source where the incident angle is the first angle, and performing radiographic imaging a number of times that is less than the plurality of times at each position of the radiation source where the incident angle is one of the second angles.

11. A non-transitory storage medium storing a program that causes a computer to execute radiographic image acquisition processing, the radiographic image acquisition processing comprising:
moving a radiation source, and controlling an incident angle of radiation with respect to a detection face of a radiation detector so as to be a plurality of angles including a first angle where an incident direction of radiation with respect to the detection face is a direction of a normal line to the detection face, and a plurality of second angles different from the first angle; and
performing radiographic imaging a plurality of times at a position of the radiation source where the incident angle is the first angle, and performing radiographic imaging a number of times that is less than the plurality of times at each position of the radiation source where the incident angle is one of the second angles.

* * * * *